(12) United States Patent
Kuri-Harcuch et al.

(10) Patent No.: US 6,582,696 B2
(45) Date of Patent: Jun. 24, 2003

(54) WOUND REPAIR DRESSINGS AND METHODS FOR THEIR PRESERVATION

(75) Inventors: Walid Kuri-Harcuch, Brookline, MA (US); Federico Castro Munozledo, Chapultepec (MX); Luis Salazar-Olivio, Texcoco (MX); Meytha Marsch-Moreno, Brookline, MA (US)

(73) Assignee: Celadon Science, LLC, Brookline, MA (US)

( * ) Notice: Subject to any disclaimer, the term of this patent is extended or adjusted under 35 U.S.C. 154(b) by 0 days.

(21) Appl. No.: 10/175,939

(22) Filed: Jun. 20, 2002

(65) Prior Publication Data

US 2002/0192197 A1 Dec. 19, 2002

Related U.S. Application Data

(63) Continuation of application No. 08/817,864, filed as application No. PCT/US95/14648 on Nov. 9, 1995, which is a continuation-in-part of application No. 08/337,162, filed on Nov. 9, 1994, now abandoned.

(51) Int. Cl.[7] .................. A01N 63/00; A61E 13/00; A61L 15/00; A61L 15/16
(52) U.S. Cl. ................ 424/93.7; 424/443; 424/445; 424/447
(58) Field of Search ............... 424/93.7, 443, 424/445, 447

(56) References Cited

U.S. PATENT DOCUMENTS

| | | | |
|---|---|---|---|
| 4,856,871 A | 8/1989 | Van Sant | 350/253 |
| 5,145,770 A | 9/1992 | Tubo et al. | |
| 5,197,985 A | 3/1993 | Caplan et al. | |
| 5,358,931 A | * 10/1994 | Rubinsky et al. | |
| 5,405,742 A | 4/1995 | Taylor | |
| 5,440,018 A | 8/1995 | Ohumra et al. | |
| 5,518,878 A | 5/1996 | Wilkins et al. | |
| 5,580,714 A | 12/1996 | Polovina | |
| 5,580,781 A | 12/1996 | Naughton et al. | |

FOREIGN PATENT DOCUMENTS

| | | |
|---|---|---|
| WO | WO 94/13135 | 6/1994 |
| WO | WO 96/14738 A2 | 5/1996 |

OTHER PUBLICATIONS

Reiners et al. "Cryopreservation of human granulocyte–macrophage progentor cells (CFU–c) with dimethyl sulfoxide (DMSO) and human serum albumin", Cryo–Letters (1986) 7: 327–337, 1986.*
Story "Biochemistry of natural freeze tolerance in animals: molecular adaptations and application to cyropreservation" Biochem. Cell Biol. (1990) 68(4): 687–698, Apr. 1990.*
*Registry of the Effects of Chemical Substances*, (1985–1986)—A Comprehensive Guide.

* cited by examiner

Primary Examiner—Michael V. Meller
(74) Attorney, Agent, or Firm—Wolf, Greenfield, & Sacks, P.C.

(57) ABSTRACT

Methods and products relating the preservation of cultured mammalian epithelial or mesenchymal cells are provided. The methods involve the pre-treatment of epithelial cells with a solution containing a cryoprotectant amount of monosaccharides and/or disaccharides. The treated cells then are frozen, dried or freeze-dried in a minimum volume of solution and stored for later use. The invention avoids the use of materials that must be washed away from the preserved tissue prior to application of the tissue to a wound bed. The invention also permits the storage of epithelial tissue in a dry state.

7 Claims, No Drawings

WOUND REPAIR DRESSINGS AND METHODS FOR THEIR PRESERVATION

This application is a Continuation of prior application Ser. No. 08/817,864, filed on Sep. 4, 1997, entitled WOUND REPAIR DRESSINGS AND METHODS FOR THEIR PRESERVATION, which is a National Stage of PCT/US95/14648, filed on Nov. 9, 1995, which is a continuation-in-part of U.S. application Ser. No. 08/337,162, filed on Nov. 9, 1994 now ABN.

FIELD OF THE INVENTION

This invention relates to methods of cryopreserving sheets of cultured epithelial cells and related products deriving therefrom.

BACKGROUND OF THE INVENTION

A major achievement in animal cell technology consists in the establishment of optimal conditions for cryopreservation of living cells and tissues, since long-term storage of valuable materials is enhanced. With cryopreservation, the intrinsic technical or practical difficulties associated with handling biomaterials such as (i) the limited shelf-life of isolated tissues, and (ii) the limited availability of tissues as source of cells for research and clinical applications, are reduced or avoided. From this point of view, development of preservation protocols for living cells and tissues has acquired remarkable importance for tissues susceptible for transplantation.

After early work on cryopreservation, that reported the successful use of glycerol to prevent damage of cells during freezing (Polge et al, 1949, Nature 164:666), several strategies to preserve cell and tissue structure, viability and metabolism have been attempted. The methods of preserving cells and tissues include: special isotonic buffered solutions; specific thawing schedules; the use of cryoprotectant agents; and approaches that comprise slow, rapid or ultrarapid freezing; all in order to prevent the otherwise inevitable destruction of living samples by handling. In general, when freezing methods are used, a major factor responsible for tissue damage is phase change (liquid to crystalline solid water), since ice formation is accompanied by changes in electrolyte concentration and pH, dehydration, and other factors not understood. These deleterious effects have been reduced by addition of cryoprotective agents and by carefully controlled freezing protocols.

Cryoprotective agents fall into two categories. One category acts by permeating the cell membrane and reducing the intracellular water concentration (e.g. glycerol, dimethyl sulfoxide (DMSO), and monosaccharides such as mannose, xylose, glucose, ribose and fructose). The other is non-permeating agents, the mechanism of action of which is not clear. Commonly employed non-permeating cryoprotectants include polyvinyl-pyrrolidone (PVP), hydroxyethyl starch (HES), disaccharides (such as sucrose), and sugar alcohols (polyalcohols such as mannitol). Recently, freezing protocols which combine both permeating and non-permeating agents have been developed.

Freezing of isolated cells has become routine with glycerol and DMSO being the predominate cryoprotectants (Coriell, L. L., 1979, Methods in Enzymology LVIII, pages 29–36; Doyle et al, 1994, Cell & Tissue Culture: Laboratory Procedures. J. Wiley & Sons, pages 4C: 1. 1–4C:2.4). Animal embryos also have been successfully preserved in the presence of glycerol (Whittingham et al, 1972, Science 178:411–414; Niemann et al, 1993, Mol. Reprod. Develop. 36:232–235). Drying and freeze-drying, on the other hand, have given excellent results only when used to preserve biomaterials other than living mammalian cells or tissues. For example, freeze-drying is now extensively used for proteins, protein mixtures and bacteria; however, the first attempts for lyophilization of mammalian cells and tissues were unsuccessful (Greaves, R. I. N., 1960, Ann. N.Y. Acad. Sci. 85:723–728). The recent discovery of biochemical adaptations of living organisms to survive complete dehydration (anhydrobiosis) (Crowe & Madin, 1975, J. Exp. Zool. 193:323–334; Womersley & Smith, 1981, Comp. Biochem. Physiol. 70B:579–586; reviewed by Womersley, 1981, Comp. Biochem. Physiol. 70B:679–678) or freezing (Constanzo et al, 1993, J. Exp. Zool. 181:245–255; King et al, 1993, Am. J. Physiol. 265:R1036–R1042; Karow et al, 1991, BioScience 41:155–160; Storey, 1990, Am. J. Physiol. 258:R559–R568), suggested new methods for preservation of mammalian cells or tissues.

It is believed that carbohydrates (such as trehalose, lactose, maltose, cellobiose, sucrose, glucose, fructose, among others) and polyols (such as sorbitol and myo-inositol) might confer dehydration protection (Womersley & Smith, supra) and freeze-tolerance (Storey & Storey, 1988, Physiol. Rev. 68:27–84), in part through water replacement around cell membranes (Crowe et al, 1984, Arch. Biochem. Biophys. 232:400–407; Crowe et al, 1984, Biochem. Biophys. Acta 769:141–150). One of the most interesting carbohydrates that might be involved in dehydration-resistance and freeze-tolerance is glucose. This monosaccharide, possessive of extremely important functions in the metabolism of vertebrate cells, appears to have an important role in freeze-tolerance in a variety of frog species (King et al, 1993, supra; Constanzo et al, 1993, supra; Storey & Storey, 1988, supra). Data obtained from analysis of freeze-tolerant species suggest that during freezing of those animals (i) blood concentration of glucose increases significantly; (ii) glucose might be as an energy source in the anoxic and ischemic state imposed by the freezing; and (iii) glucose might function as a metabolic depressant (Storey & Storey, 1988, supra).

Sucrose has been used as a component in cryopreservation solutions used for corneal tissue storage (Madden et al, 1993, Cryobiology 30:135–157; Rich & Armitage, 1991, Cryobiology 28:159–170; McCarey et al, 1973, Cryobiology 10:298–307) and embryonic tissue freezing (Isachenko et al, 1993, Cryobiology 30:432–437). Also glucose and other carbohydrates have been used for red blood cell lyophilization (Goodrich et al., U.S. Pat. Nos. 4,874,690; 5,171,661 and 5,178,884). However, red blood cell preservation does not require maintenance of tissue-type structural organization, which would be required for tissue transplantation. In the above methods, red blood cell viability has been determined only by quantitation of erythrocyte lysis, hemoglobin recovery, or assay of glycolytic enzymes (see Goodrich et al, U.S. Pat. Nos. 4,874,690 and 5,178,884), but not by parameters related to cell integrity and tissue organization, such as protein synthesis and secretion.

Green and collaborators described a method for culturing human epidermal keratinocytes (Rheinwald & Green, 1975, Cell 6:331–343), that has been extended to other cultured epithelial cells. Under such culture conditions, stratified epithelial sheets suitable for transplantation onto large burn surfaces, ulcerations and other skin wounds are obtained (Gallico et al, 1984, New Eng. J. Med. 311:448–451; Heighten et al, 1986, J. Am. Acad, Dermatol. 14:399–405). The cultured epithelia obtained through this procedure have also been used as allografts for temporary wound dressing (T. J. Phillips et al., 1989, J. Am. Acad. Derm. 21:191; Bolivar-Flores et al, 1990, Burns 16:3–8). Epithelial cell cultures have become a powerful tool for body surface reconstruction, however, their limited shelf-life has restricted their use to those medical facilities that are not too far away from the production facility. After dispase detachment of epithelial sheets for transportation to the hospital, shelf-life is short. Therefore, the establishment of a preservation method for the cultured sheets should permit their banking and also, their shipment worldwide. In this regard, some strategies have been attempted. Several authors have developed cryopreservation methods based on the use of glycerol or dimethyl sulfoxide as cryoprotectants, following a specific freezing protocol (see Cancedda and De Luca, 1994, U.S. Pat. No. 5,298,417). Others have cryopreserved cultured epithelial sheets with media containing both cell-penetrating glass-forming agents (specifically glycerol) and non-penetrating protectant agents (preferably polyvinylpyrrolidone (PVP), dextran or hydroxyethyl starch) (see Tubo et al, 1992, U.S. Pat. No. 5,145,770). However, these methods require a specific and elaborate freezing protocol, and a thawing protocol that appears to impose difficulties in the wide use of these tissues in the clinical field; or a possible impairment of the medical efficacy due to difficulties in the thawing and rinsing protocols required in order to use such epithelial sheets.

SUMMARY OF THE INVENTION

The present invention provides methods and products for preserving cultured epithelial and mesenchymal cells for wound repair. It permits the use of preserved tissue without the need to wash away cryopreservation components. It also avoids the need for cumbersome handling, freezing and thawing protocols characteristic of the prior art. The invention further permits storage of preserved cells at higher temperatures relative to the prior art and even permits dry preservation and storage of tissue. All of the foregoing is accomplished while maintaining the structural and functional characteristics necessary to permit use of the preserved cells in wound repair in a patient. Cell functions such as protein synthesis and secretion of cellular products (e.g. growth factors and extracellular matrix components) are about the same as or even better than those activities characteristic of cells or tissues frozen by standard methods.

According to one aspect of the invention, a method for preserving cultured mammalian or mesenchymal epithelial cells is provided. The cells are incubated in a solution containing a cryoprotectant amount of a monosaccharide or a disaccharide. Excess solution then is removed from said cells, and the cells are preserved in the presence of said cryoprotectant amount by freezing, drying or freeze-drying. Preferably, the cells are a sheet of cultured epithelial keratinocytes. In one embodiment, the cells are human cells. Preferably, the excess solution is removed by aspiration or by draining. In such instances, the solution is present at no more than 30 ml per 50 cm$^2$ of the sheet of cultured keratinocytes, and more typically is present in such small amounts so as to be impractical to measure.

A preferred incubation solution contains between 0.05 and 3.5 M glucose and between 0.1 mg and 40 mg per ml of human serum albumin. Most preferably, the solution is free of amounts of exogenous materials that would interfere with wound healing when applied to a wound bed and that must be washed from the cells prior to application to a wound bed. Thus, the solution may be free of materials such as DMSO, PVP, glycerol and nonhuman serum albumin.

According to another aspect of the invention, products made according to the foregoing methods are provided. One such product is a graftable tissue. The tissue is cultured mammalian epithelial or mesenchymal cells, and in a preferred embodiment is a sheet of cultured epithelial cells. The cells are surrounded by an extracellular phase, wherein the extracellular phase contains a cryoprotectant amount of a monosaccharide or a disaccharide. The extracellular phase also may be free of materials that interfere with wound healing or that must be washed from the tissue when applied to a wound bed, as described above. The cells, for example, may be frozen in a minimum volume of solution containing the monosaccharide and/or disaccharide. Likewise, the cells may be dried or freeze-dried.

According to another aspect of the invention, a cryopreserved wound repair tissue is provided. The tissue is frozen cultured mammalian epithelial or mesenchymal cells which, after being stored at between –20° C. and –70° C. for three, six or even more months, when applied to the surface of the wound in a patient, maintain structural and functional characteristics sufficient to induce wound healing in a patient. The cells preferably are a sheet of confluent, cultured epithelial cells.

Another aspect of the invention is dry cultured mammalian epithelial or mesenchymal cells which, after being stored in such a dry state and applied to the surface of a wound in a patient, maintain structural and functional characteristics sufficient to induce wound healing in a patient. Again, a sheet of confluent, cultured mammalian epithelial cells represents a preferred embodiment. According to this aspect of the invention, the material may be applied in a dry state to the wound or may be rehydrated in advance of its application to the wound. Thus, the invention also involves methods for treating a patient including any of the foregoing products, and in particular includes, but is not limited to, application of a dried sheet of cultured epithelial cells to a wound bed.

The cryopreservative solutions of the invention may include, in addition to monosaccharides and/or disaccharides, other cryoprotective agents, including, but not limited to, proteins or mixtures of proteins as additional protective agents. For example, the solution may contain whole serum or serum albumin, as well as any other penetrating and non-penetrating cryoprotective agents useful in maintaining and protecting tissue viability, structure and/or metabolic activity. In one preferred embodiment, human keratinocytes are cultured in a cryoprotective solution including glucose and human serum albumin, wherein the solution is free of any cryoprotective agent that would have to be washed away prior to application of the cultured cells to a wound bed. Thus, the invention contemplates thawing of a frozen sheet of epithelial cells and application of that sheet to a wound bed without the need for any washing after thawing and prior to application to the wound bed.

The cultured epithelial cells may be attached, or not, to substrata and combined with a backing material, if desirable. Thus, the invention contemplates preservation of cultured epithelial sheets, skin equivalents, mesenchymal-derived tissues and/or cultured cells. The invention also permits one-step and two-step simple freezing protocols with subsequent banking and storage of the tissues. If the tissue is dried, then it can be stored even at room temperature, although lower temperatures are desired. If the tissue is frozen, the tissue may be stored at –20° C., although lower temperatures may be desirable.

These and other aspects and features of the invention will be described in greater detail below.

DETAILED DESCRIPTION OF THE INVENTION

The present invention involves a novel method for preserving either (i) cultured epithelial sheets obtained by culturing epidermal keratinocytes, corneal keratinocytes or other epithelial cell types; (ii) cultured but non-confluent epithelial cells; (iii) skin substitutes, equivalents or the like (understanding skin equivalent as a epithelial sheet obtained by culture of epidermal keratinocytes onto a gel made of extracellular matrix components such as collagen or hyaluronic acid or a dermal equivalent such as de-epidermized dermis and containing mesenchymal cells or not); or (iv) mesenchymal-derived cells or tissues for wound repair. Cells useful for wound repair of a human patient are particularly contemplated. Cells of the foregoing type may be cultured, detached or not, with substratum, and combined, with or without, a backing material. Examples of substratum are well known to those skilled in the art and include gels, films and extracellular matrices such as hyaluronic acid, collagen, fibrin glue and synthetic products. Backing materials, likewise, are known to those skilled in the art and include gauze, plastics, silicones, hydrogels and dextran.

The tissue sample to be preserved first is incubated in a solution that may be a nutrient medium or an isotonic solution containing a cryoprotectant amount of a monosaccharide or a disaccharide. After a period of incubation, typically between about 5 minutes and 8 hours at room temperature, the excess solution then is removed from the cells and the cells are frozen, dried or freeze-dried in the presence of the cryoprotectant.

A cryoprotectant amount of a monosaccharide or a disaccharide is that amount of a monosaccharide alone, a disaccharide alone or a mixture of monosaccharides and/or disaccharides which will permit the cryopreservation of epithelial or mesenchymal cells according to the methods of the invention without the need of exogenous cryopreservation agents that interfere with wound healing when applied to a wound bed. For example, DMSO and PVP are used routinely in a cryopreservation but are always washed from tissue grafts prior to application of the graft to the wound bed. The present invention permits cryopreservation without such agents, thereby avoiding the need for extra, unnecessary washing steps. In the case of the preferred monosaccharide, glucose is used at concentrations between about 0.05M and 3.5M. The lower limit is about 8–10 times greater than the concentration of glucose in blood, extracellular fluid or typical nutrient media (0.0055 M) and is about twice as much as is present in nutrient media with the highest levels of glucose (0.025 M). The preferred amount of glucose is on the order of between 0.1 M and 1 M. The preferred amounts of other monosaccharides and disaccharides will depend upon the particular conditions employed, particular cells cultured and upon the presence and concentration of any other biocompatible protective agents such as human serum or human serum albumin. In all cases, cryoprotectant amounts exceed by at least two times those amounts of monosaccharides and disaccharides present in nutrient media and the like.

The solutions of the invention preferably are free of amounts of exogenous materials that interfere with wound healing when applied to a wound bed. Such exogenous materials are well known to those skilled in the art and include materials commonly used as cryoprotective agents. For example, DMSO, PVP and polyhydroxy carbohydrates are often used as cryoprotective agents. It is common practice to remove such agents from the thawed tissue by washing prior to applying the tissue to a wound bed. Likewise, dextran and nonhuman sources of protein including albumin are used in cryopreservation protocols and are thoroughly removed prior to applying the preserved tissue to a wound bed. On the other hand, materials such as human serum albumin, proline, spermine, myristic acid, low concentrations of zinc and many other cryopreservative agents do not interfere with wound healing. Thus, the present invention in its preferred embodiments contemplates biocompatible preservation solutions that do not cause additional wash steps prior to application of the preserved tissue to a wound bed.

The invention contemplates preserving the tissue in a minimum volume of solution. This is a departure from the prior art and is an advantage of the present invention. One advantage is simplified handling, whereby the tissue can be placed in bags or dishes and preserved without concern for spillage, without the need for sealed dishes and without other cumbersome protocols characteristic of the prior art. An unexpected advantage is the ability to freeze-dry cultured cells and tissue using the cryoprotective agents of the invention. In particular, the present invention permits sheets of epithelial cells to be freeze-dried, stored, rehydrated (or not) and used in wound repair. Storage can be at relatively high temperatures, permitting shipment and use in remote locations and avoiding the need for expensive, space-limited −70° C. freezer space. Freeze drying is facilitated by removing as much cryoprotectant solution as practicable prior to freezing; with a minimum volume of fluid, freezing, drying and thawing proceeds quickly and with minimal functional damage to cells. The present invention thus provides a preserved epithelial wound repair tissue comprising a dry, confluent sheet of cultured epithelial cells which, after being stored in a dry state and applied to the surface of a wound in a patient, maintains structural integrity and functional characteristics sufficient to induce wound healing in a patient.

Minimum volumes can be achieved by aspirating excess solution and/or by gravity-draining solution from the cells. Other methods will be apparent to those skilled in the art. It is desirable to have no more than 30 ml solution per graft of 50 $cm^2$ of tissue although even lower amounts are preferred.

Cryoprotective agents useful according to the invention include permeant and non-permeant agents, as well as agents which must be washed off prior to application of the preserved tissue to a wound bed (although agents that are biocompatible are preferred). Agents known to be useful as cryoprotectants include the following: monosaccharides (e.g. glucose, fructose, maltose, ribose, mannose, xylose); disaccharides (e.g. trehalose, sucrose, cellobiose, lactose); trisaccharides (e.g. raffinose); sugar alcohols (e.g. mannitol, sorbitol, myo-inositol, phosphorylated inoitols, glycerol); polysaccharides (e.g. hydroxyethyl starch (HES), dextran, phosphorylated dextran, heparine, heparan sulphate, hyaluronic acid, dermatan sulphate, chondrollin sulphate, agarose); carboxylic acids (e.g. pyruvate, 2,3,-diphosphoglycerate); protein and protein mixtures (e.g. blood, animal serum, plasma, human albumin, bovine albumin, bovine gelatin, fish gelatin).

The preferred cryopreservative solution includes a monosaccharide and a protein or a mixture of protein. The preferred monosaccharide, glucose, is added at a concentration of between 0.05 and 3.5M, and the protein or protein mixture is added at a concentration of between 0.1 and 40.0 mg/ml. Most preferably, the solution consists of nutrient media containing between 0.1 and 1.0M glucose plus 1.0–5.0 mg per ml human serum albumin (or 0.05–40 mg/ml serum, most preferably human). The material to be preserved is immersed in the solution at a temperature range between 5° C. and 40° C. and preferably at room temperature. The time of incubation is between about 5 minutes and 8 hours, although longer periods are possible, but not necessarily desirable. After the incubation, the material is frozen in the minimum volume of solution remaining after total aspiration or gravity-draining leaves no more than about 30 ml of solution per 50 cm$^2$ of tissue and, more typically, leaves minimum volumes (i.e. amounts so low as to be impractical to measure). The material may be frozen, freeze-dried or dried.

Conventional freezing, freeze-drying and drying protocols may be employed. An advantage of the present invention is that any of the known protocols for freezing are useful according to the present invention. A simple two-step procedure has been found to be particularly suitable, wherein the cultured epithelial sheets are first maintained at a temperature of about −20° C. for 5 to 12 hours, after which the cells are frozen to −80° C. over the course of about 2 hours. The frozen material then may be stored or banked at such temperatures. It should be understood, however, that the material may be frozen in a one-step procedure to a temperature of −20° C. and stored or banked at that temperature. Cultured epithelial sheets have been successfully maintained either at −20° C. or −80° C. for a year.

According to one aspect of the invention, the cultured epithelial sheets are freeze-dried. The resultant material represents the first cultured epithelial sheets preserved in a dry state which, after being stored for even an extended period of time, can be applied to the surface of a wound, maintaining the structural integrity and functional characteristics sufficient to induce wound healing. As mentioned above, it is even possible to apply the dried epithelial sheet directly to the wound, allowing the body fluids to rehydrate the epithelial sheet.

When freeze-drying, conventional procedures are employed except that monosaccharides and/or disaccharides are used as cryoprotectants and the cells are frozen in a minimum volume of cryoprotectant solution. Thus, the epithelial sheets can be frozen by cooling, for example, to −70° C. for about 20 minutes, and, subsequently, the frozen epithelia can be lyophilized in conventional equipment. The freeze-dried epithelial sheets then may be maintained in heat-sealed bags and banked or stored, for example, at 4° C. This is the first known example of freeze-drying of cultured epithelial cells to result in a useful wound repair product.

Alternatively, the cells may be dried at a range of temperatures without freezing.

Under the foregoing storage conditions, the in vitro generated tissue maintains a biosynthetic activity about the same as or higher than that found in tissue preserved by the methods of the prior art. Structural integrity, protein synthesis and cell secretion ability is maintained similar to or higher than the corresponding features in cells preserved by methods known in the art.

Because the preferred preservative solutions employ cryoprotectants that are not toxic and not immunogenic, the rinsing of cultured cells, cultured epithelial sheets or skin equivalents typical of prior art methods is obviated. Likewise, because a minimum of solution is used in the freezing process, thawing occurs in a minimum amount of time (as little as in a minute), by allowing the material to warm up in a 37° C. bath. The material, of course, can be directly immersed into a thawing medium.

The following specific examples will illustrate the procedures of the invention, when applied to the preservation of cultured epidermal sheets. However, as described above, the same procedures are extended for preservation of cultured epithelial sheets (obtained by culture of human or nonhuman epithelial cells from epidermis, cornea or another epithelial cell types), skin substitutes or other cultured cell types.

EXAMPLE I

Epidermal sheets were obtained by culturing human neonatal foreskin keratinocytes, using the procedures developed by Rheinwald & Green (1975, supra).

The epithelial sheets were detached from culture dishes using Dispase 11 (Boehringer Mannheim) at a final concentration of 2.5 mg/ml. After detaching from culture dishes, the epithelial sheets are washed with phosphate buffered saline (PBS) at room temperature, mounted in a backing material, and incubated for 10 minutes with preservation solution consisting in Dulbecco-Vögt modification of Minimal Esential Medium (DMEM) containing glucose and human serum albumin at the indicated concentrations; if desired, preservation solution may be buffered, % Nith 20.O mM HEPES. After incubation, the preservation solution is aspirated leaving the minimum volume of solution in the vessel containing the epithelium. Afterwards, epithelia, which may be mounted on a backing material, are kept in heat-sealed bags and frozen following a two-step procedure: First, they are maintained at −20° C. during 5 hours; then cooled overnight to −70° C. Finally, the frozen epithelia are banked or stored at −70° C.

Epithelial sheets were thawed in culture medium (Dulbecco-Vögt modification to Minimum Essential Medium, DMEM) or in buffered saline containing trehalose and serum albumin, and viability was determined by quantification of [$^{35}$S]-methionine incorporation into protein released to culture medium. The thawed epithelia were incubated with low methionine (6 μg/ml) DMEM containing [$^{35}$S]-methionine (4.0 μCi/ml) at 37° C., and radioactivity incorporated into TCA percipitable material was determined in aliquots of culture medium.

Table I shows the results obtained in this experiment. To normalize radioactivity incorporation values, cultured epithelial sheets used as controls were incubated with DMEM containing 10% (v/v) animal or human serum and 10% (v/v) glycerol (standard procedure) for 10 minutes, and frozen following the above two-step procedure. After thawing, epithelial viability was determined by measuring the [$^{35}$S]-methionine incorporation into released protein, and results from these control epithelia were referred as the unit. It is shown the mean value from triplicate epithelia.

TABLE I

Cryopreservation of cultured epidermal sheets by the invented procedure.

| Cryopreservation solution | Protein Synthesis and Release by Epithelial Sheet (normalized) |
|---|---|
| DMEM + 10% (v/v) animal serum + 10% (v/v) glycerol (CONTROL) | 1.00 |
| DMEM + 0.5M glucose + 5.0 mg/ml serum albumin | 1.95 |
| DMEM + 0.5M glucose + 20 mg/ml serum albumin | 1.40 |
| DMEM + 0.25M glucose + 20 mg/ml serum albumin | 1.59 |
| DMEM + 2.0M glucose + 5.0 mg/ml serum albumin | 1.32 |

EXAMPLE II

In other experiments, after incubation in preservation solution, epithelia were lyophilized or dried. Cultured epithelial sheets are detached, mounted in a backing material and incubated in the preservation solution as above. The preservation solution is aspirated, leaving the minimal volume of solution at the vessel containing the epithelium. Then, epithelia are frozen by cooling at −70° C., at least for 20 minutes. Afterwards, frozen epithelia are lyophilized in a Lyphlock 6 Freeze dry/Shell freeze system (Labconco). The freeze-dried epithelia can be kept in heat-sealed bags and banked or stored at 4° C. After preservation for at least 48 h, epithelia were reconstituted by immersion in DMEM, and epithelial viability was assayed as described at Example 1. Results are shown at Table II. In this illustrative experiment, [$^{35}$S]-methionine incorporation values were also normalized, using epithelial sheets frozen after preincubation with DMEM plus 10% (v/v) FBS and 10% (v/v) glycerol as references. Similar results were obtained when other solutions such as phosphate buffered saline, or isotonic saline containing serum albumin and/or mono- or disaccharides, were used for reconstitution of the epithelial sheets, skin equivalents or cells.

TABLE II

Freeze-drying of protected cultured epidermal sheets.

| Preservation solution | Protein Synthesis and Release by Epithelia Sheet (normalized) |
|---|---|
| DMEM + 0.5M glucose + 20.0 mg/ml serum albumin | 0.80 |
| DMEM + 0.5M glucose + 10.0 mg/ml serum albumin | 0.72 |

EXAMPLE III

Since the way to determine cell viability by cell growth parameters or specific dye staining, requires trypsinization of the cell sheet into single cells, and since this procedure of trypsinization by itself causes cell damage and decreases cell viability and cell growth ability, cultured human epidermal keratinocytes were harvested during exponential growth phase using a (1:1) mixture of trypsin 0.15% and EDTA 0.02%. Cells were extensively washed with culture medium and pelleted. Then, cells were resuspended and incubated with preservation medium. After incubation cells were frozen following the two-step procedure described above, or freeze-dried as in the Example II. The cryopreserved cell suspensions were stored at temperatures about −20° C. or lower, and freeze-dried cells were stored at ambient or lower temperatures at least during 24 hours. Cells were thawed or reconstituted with culture medium, and aliquots were used to determine cell viability by trypan blue dye exclusion. Results from this type of experiment are shown.

TABLE III

Preservation of keratinocyte suspensions by freezing or freeze-drying.

| Preservation solution | Cells Excluding Trypan Blue (%) |
|---|---|
| a) Frozen cells | |
| DMEM + 10% (v/v) animal serum + 10% (v/v) glycerol (CONTROL) | 97.15 +/− 0.15 |
| DMEM + 0.5M glucose + 5.0 mg/ml serum albumin | 93.10 +/− 0.80 |

TABLE III-continued

Preservation of keratinocyte suspensions by freezing or freeze-drying.

| Preservation solution | Cells Excluding Trypan Blue (%) |
|---|---|
| b) Freeze-dried cells | |
| DMEM + 10% (v/v) animal serum + 10% (v/v) glycerol (CONTROL) | 66.00 +/− 0.58 |
| DMEM + 0.5M glucose + 5.0 mg/ml serum albumin | 80.30 +/− 2.82 |

EXAMPLE IV

In similar experiments to those shown in Example III, human epidermal keratinocytes were harvested, washed, and after pelleting, cells were resuspended and incubated with preservation medium consisting of DMEM plus 0.005M to 3.5M glucose, plus 0.1 mg/ml to 40.0 mg/ml serum albumin plus either 1.0%. 10%, (v/v) glycerol or 1% −10% (v/v) DMSO. After incubation, cells were frozen following the step procedure described above or freeze-dried as in the Example II. The cryopreserved cell suspensions were stored at temperatures about −20° C. or lower, and freeze-dried cells were stored at ambient or lower temperatures at least 24 hours. Cells were thawed or reconstituted with culture medium, and cultured to determine cell proliferation abilities. The results obtained from these experiments are as shown in Example I.

The procedures illustrated above were successfully employed for the preservation of cultured epithelial sheets or epithelial cell suspensions either by freezing, freeze-drying or drying.

In all cases, the dressings, cells or tissue samples were incubated with cryopreservation solutions containing either glucose (0.005M to 3.5M) and serum albumin (0.1 mg/ml to 40.0 mg/ml) or glucose (0.005M to 4.0M) and animal or human serum (0.05 mg/ml to 40.0 mg/ml), or glucose (0.005M to 3.5M) plus serum albumin 0.1 to 40.0 mg/ml DMSO (1%−10%) or glycerol (1%−10%).

The disclosed methods ensure cell/tissue structural integrity and metabolic activities such as protein synthesis and release (as examples of growth factors or extracellular matrix components). These procedures are useful to preserve epithelial sheets obtained by culture of human or nonhuman epithelial cells from epidermis, cornea or other epithelial cell types, skin substitutes or another cultured cell types; therefore, they should be valuable for multiple fields such as therapeutic, pharmacological and also for research.

Various modifications and equivalents will be apparent to those skilled in the art.

What is claimed is:

1. A method for treating a wound with a thawed sheet of cultured mammalian epithelial cells comprising
    a) providing a sheet of cultured mammalian epithelial cells that was frozen to produce a frozen sheet of cultured mammalian epithelial cells;
    b) thawing the frozen sheet of cultured mammalian epithelial cells wherein the frozen sheet of cultured mammalian epithelial cells has been frozen in contact with a cryoprotectant solution comprising a cryoprotectant amount of a cryoprotectant selected from the group consisting of monosaccharides, disaccharides, and mixtures thereof, wherein the cryprotectant solution is free of amounts of exogenous materials that would interfere with wound healing when applied to a wound and free of exogenous amounts of materials that must be washed from the frozen sheet of cultured mammalian epithelial cells prior to application to a wound to produce a thawed sheet of cultured mammalian epithelial cells, and c) applying the thawed sheet of cultured mammalian epithelial cells to the wound, wherein the thawed sheet of cultured mammalian epithelial cells is applied to the wound without washing the thawed sheet of cultured mammalian epithelial cells.

2. The method of claim 1 wherein the cyroprotectant solution is free of dimethyl sulfoxide, polyvinylpyrrolidone, glycerol and nonhuman serum albamin.

3. The method of claim 1 wherein the cells were frozen in a minimum volume of cryoprotectant solution before thawing.

4. The method of claim 1 wherein the cryoprotectant solution contains a cryoprotectant amount of glucose.

5. The method of claim 4 wherein the cryoprotectant amount of glucose is between about 0.05 and 3.5 M glucose.

6. The method of claim 2, 3, 4, 5, or 1 wherein the cells are cultured on a substratum.

7. The method of claim 2, 3, 4, 5, or 1 wherein the cells are combined with a backing material prior to application to the wound bed.

* * * * *